(12) United States Patent
Ahn et al.

(10) Patent No.: US 11,162,077 B2
(45) Date of Patent: Nov. 2, 2021

(54) APICIDIN-CONTAINING COMPOSITION FOR INDUCING DIFFERENTIATION OF MESENCHYMAL STEM CELLS INTO CARDIAC-COMMITTED CELLS

(71) Applicant: CHONNAM NATIONAL UNIVERSITY HOSPITAL, Gwangju (KR)

(72) Inventors: Youngkeun Ahn, Gwangju (KR); Yong Sook Kim, Gwangju (KR); Dong Im Cho, Gwangju (KR)

(73) Assignee: CHONNAM NATIONAL UNIVERSITY HOSPITAL

( * ) Notice: Subject to any disclaimer, the term of this patent is extended or adjusted under 35 U.S.C. 154(b) by 62 days.

(21) Appl. No.: 15/767,151

(22) PCT Filed: May 9, 2016

(86) PCT No.: PCT/KR2016/004789
§ 371 (c)(1),
(2) Date: Apr. 10, 2018

(87) PCT Pub. No.: WO2017/065370
PCT Pub. Date: Apr. 20, 2017

(65) Prior Publication Data
US 2018/0298339 A1 Oct. 18, 2018

(30) Foreign Application Priority Data
Oct. 12, 2015 (KR) .......................... 10-2015-0142342

(51) Int. Cl.
*C12N 5/077* (2010.01)
*A61K 35/34* (2015.01)
*A61K 31/454* (2006.01)
*A61K 35/28* (2015.01)
*A61K 31/395* (2006.01)
*A61K 9/00* (2006.01)

(52) U.S. Cl.
CPC .......... *C12N 5/0657* (2013.01); *A61K 31/395* (2013.01); *A61K 31/454* (2013.01); *A61K 35/28* (2013.01); *A61K 35/34* (2013.01); *C12N 5/0653* (2013.01); *C12N 5/0654* (2013.01); *A61K 9/0019* (2013.01); *C12N 2501/065* (2013.01); *C12N 2501/999* (2013.01); *C12N 2506/1353* (2013.01)

(58) Field of Classification Search
None
See application file for complete search history.

(56) References Cited

U.S. PATENT DOCUMENTS

| | | | |
|---|---|---|---|
| 2008/0019944 A1* | 1/2008 | Terzic | C12N 5/0657 424/93.1 |
| 2009/0130064 A1* | 5/2009 | Rogiers | C12N 5/067 424/93.7 |
| 2010/0173414 A1* | 7/2010 | Turovets | C12N 5/0603 435/377 |

FOREIGN PATENT DOCUMENTS

| | | |
|---|---|---|
| JP | 2007-061096 A | 3/2007 |
| KR | 10-2006-0079772 A | 7/2006 |
| KR | 10-2012-0029225 A | 3/2012 |

OTHER PUBLICATIONS

Huang et al., "Fate determination in mesenchymal stem cells: a perspective from histone-modifying enzymes", Stem Cell Research & Therapy, vol. 6, pp. 1-9. (Year: 2015).*
SAFC Biosciences, "Dulbecco's Modified Eagle's Medium/High Modified" product information; pp. 1-2 (Year: 2006).*
Feng et al., "Suberoylanilide hydroxamic acid promotes cardiomyocyte differentiation of rat mesenchymal stem cells," Experimental Cell Research, 315(17):3044-3051, 2009.
Kretsovali et al., "Histone Deacetylase Inhibitors in Cell Pluripotency, Differentiation, and Reprogramming," Stem Cells International, vol. 2012, Article ID 184154, pp. 1-10, 2012.
Choi et al., "Differentiation of human adipose-derived stem cells into beating cardiomyocytes," Journal of Cellular and Molecular Medicine, 14(4):878-889, 2010.

* cited by examiner

*Primary Examiner* — Michelle F. Paguio Frising
(74) *Attorney, Agent, or Firm* — Riverside Law LLP

(57) ABSTRACT

The present invention relates to an apicidin composition for inducing differentiation of mesenchymal stem cells into cardiac-committed cells, and a method for inducing differentiation into cardiac-committed cells using the same. The present invention allows mesenchymal stem cells to be specifically induced to differentiate into cardiac-committed cells even when an apicidin is treated for only a very short period of time of 24 hours, thereby being capable of solving the extremely low cardiomyogenic differentiation efficiency of mesenchymal stem cells, high cost, and long-term problems in the conventional art, and thus the present invention can be usefully used for treating heart disease.

4 Claims, 5 Drawing Sheets

APICIDIN-CONTAINING COMPOSITION FOR INDUCING DIFFERENTIATION OF MESENCHYMAL STEM CELLS INTO CARDIAC-COMMITTED CELLS

STATEMENT REGARDING GOVERNMENT RIGHTS

The present invention was undertaken with the support of 1) Verification of safety and superior efficacy of function-enhanced angiogenic progenitor cell in myocardial infarction porcine model, 2015M3A9B4066496 grant funded by the National Research Foundation of Korea, 2) Developing a small molecule-based novel technology to induce cardiac cells, 2015M3A9C6031684 grant funded by the National Research Foundation of Korea, and 3) Development of technique in optimized stem cell therapy and evaluation of safety to porcine myocardial infarction model, 2016R1D1A1A09917796 grant funded by the National Research Foundation of Korea.

CROSS-REFERENCE TO RELATED APPLICATIONS

This application is the U.S. national phase application filed under 35 U.S.C. § 371 claiming benefit to PCT International Application No. PCT/KR2016/004789, filed on May 9, 2016, which claims priority to Korean Patent Application Serial No. 10-2015-0142342, filed on Oct. 12, 2015, the disclosure of which is incorporated herein by reference in its entirety.

TECHNICAL FIELD

The present invention relates to an apicidin composition for inducing the differentiation of mesenchymal stem cells (MSCs) into cardiac-committed cells and a method for inducing the differentiation into cardiac-committed cells using the same.

BACKGROUND ART

Mesenchymal stem cells (MSCs) can differentiate into various cell types such as adipose cells, cartilage cells, myocytes, osteocytes, etc., and may be easily proliferated in vitro, and thus are used as a useful tool for gene therapy and cell therapy. The action mechanism of stem cells has been known to protect peripheral cells from cell death by secreting paracrine factors, inhibit an inflammatory response, and generate new blood vessels. Accordingly, for the past decades, MSC research has focused on the control of differentiation and a microenvironment, and actual clinical trials are being actively performed to verify whether MSCs can be used as a cell therapeutic agent for various diseases including bone/cartilage diseases, heart diseases, gastrointestinal diseases and immune diseases.

However, regarding the treatment of heart diseases using stem cells, problems such as very low engraftment of stem cells in the heart tissue and a loss in viability within several days may arise, and to overcome these problems, a variety of studies on priming or physiological electrical stimuli is actively progressing. Particularly, research on regeneration of lost cardiomyocytes is still very limited. While research showing that embryonic stem cells (ESCs) or induced pluripotent stem cells (iPSCs) differentiate into cardiomyocytes or cardiac-committed cells has been reported, these stem cells also become a serious obstacle to clinical application due to a low safety such as high tumorigenic potential.

Therefore, since it has been first reported that 5-azacytidine is able to induce the differentiation of MSCs into cardiac-committed cells, various efforts have concentrated on increasing the cardiomyogenic differentiation efficiency of adult stem cells. For example, there are consistent attempts to induce the cardiomyogenic differentiation of adult stem cells through the treatment of a material such as fibroblast growth factor-2, activin A, insulin or transferrin, cardiac-specific gene introduction, or a cocktail therapy (5-azacytidine+salvianolic acid B+cardiomyocyte lysis medium (CLM)).

However, there are still side effects such as the generation of variant cancers, and the composition of a cardiogenic medium that is currently used in clinical research requires various recombinant proteins and it takes 5 days or more with high costs. Therefore, despite all these efforts, an effective method for inducing the differentiation into cardiac-committed cells with fewer side effects than existing factors is hardly known yet.

Meanwhile, histone deacetylases (HDACs) have been known to inhibit histone acetylation and suppress the expression of a cell proliferation inhibitor, thereby promoting cell proliferation and controlling cell tumorization and differentiation, and thus has attracted great attention as a target for treating various diseases such as cancer or inflammatory diseases.

In addition, it has been reported that trichostatin A or valproic acid as a HDAC inhibitor induces osteogenic or neuronal differentiation of MSCs (Korean Patent Publication No. 2006-0079772), but the relationship with the differentiation into cardiac-committed cells has not been reported yet.

DISCLOSURE

Technical Problem

Therefore, the inventors identified that high-efficiency cardiomyogenic differentiation of MSCs is promoted by apicidin among HDAC inhibitors, and the present invention was completed.

The present invention is directed to providing a composition for promoting the differentiation of MSCs into cardiac-committed cells, which contains apicidin.

The present invention is also directed to providing a cell therapeutic agent for a heart disease using the composition.

The present invention is also directed to providing a method for treating a heart disease using the cell therapeutic agent.

However, technical problems to be solved in the present invention are not limited to the above-described problems, and other problems which are not described herein will be fully understood by those of ordinary skill in the art from the following descriptions.

Technical Solution

The present invention provides a composition for inducing the differentiation of MSCs into cardiac-committed cells, which contains apicidin of Formula 1 below or a pharmaceutically acceptable salt thereof as an active ingredient.

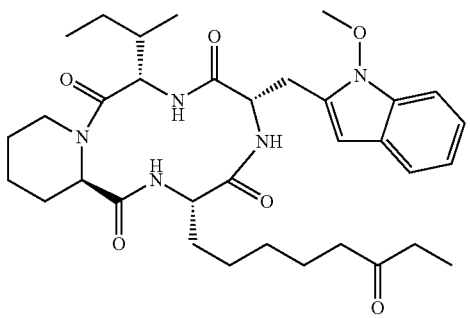

[Formula 1]

The present invention also provides a cell therapeutic agent for treating a heart disease, which contains cardiac-committed cells, whose differentiation was induced due to the composition, as an active ingredient, and a method/use for treating a heart disease using the same.

The present invention also provides a method for inducing the differentiation of MSCs into cardiac-committed cells in vitro, which includes treating isolated MSCs with the composition.

In an exemplary embodiment of the present invention, the MSCs are derived from bone marrow, adipose tissue, umbilical cord blood or peripheral blood.

In another exemplary embodiment of the present invention, the apicidin is contained at 1 to 3 µM.

In still another exemplary embodiment of the present invention, the heart disease is myocardial infarction, angina pectoris, arteriosclerosis, or arrhythmia.

Advantageous Effects

According to the present invention, even when apicidin is treated for a very short time, for example, 24 hours, MSCs can be induced to specifically differentiate into cardiac-committed cells, thus the problems of the extremely low cardiomyogenic differentiation efficiency of conventional MSCs, high cost and a long period of treatment can be resolved. For this reason, MSCs can be useful in treatment of heart diseases.

In addition, according to the present invention, since differentiation into cardiac-committed cells, rather than complete differentiation into cardiomyocytes, is induced, following myocardial implantation and engraftment, cardiomyogenic differentiation is induced in a myocardial microenvironment, and therefore the survival rate and engraftment rate of stem cells can be raised, and myocardial infarction can be improved.

MODES OF THE INVENTION

Figure 1:
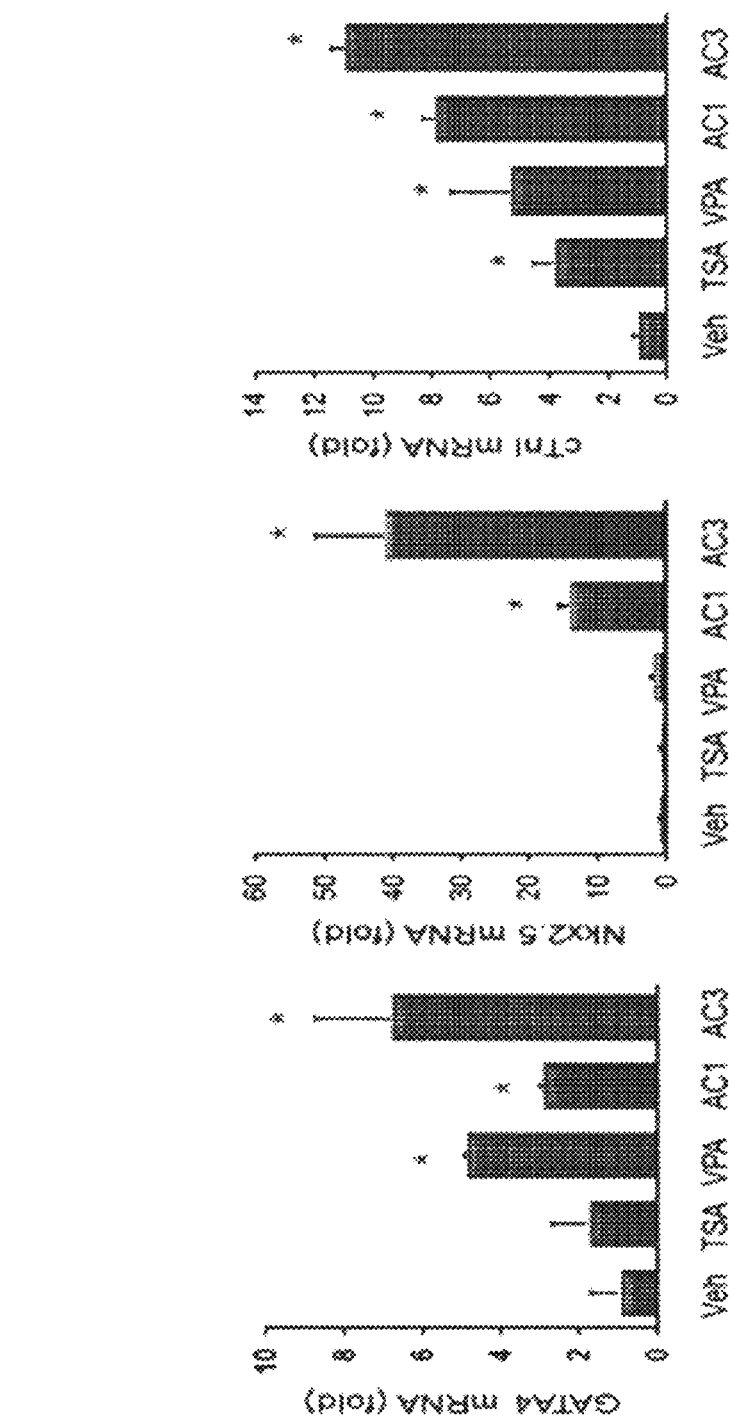
FIG. 1 shows real-time PCR results of comparing degrees of mRNA expression of cardiac-specific marker genes (GATA4, Nkx2.5, and cTnI) after MSCs are treated with HDAC inhibitors (TSA, VPA, AC and AC3). AC1: Apicidin 1 µM, AC3: Apicidin 3 µM.

The present invention provides a composition for inducing the differentiation of MSCs into cardiac-committed cells, which contains apicidin of Formula 1 below or a pharmaceutically acceptable salt thereof as an active ingredient.

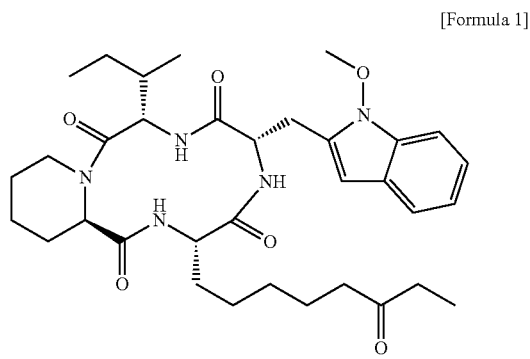 [SMILES: CCC(=O)CCCCC[C@@H]1NC(=O)[C@H]2CCCCN2C(=O)[C@H](C(C)CC)NC(=O)[C@H](Cc2cc3ccccc3n2OC)NC1=O]

[Formula 1]

The apicidin, that is, cyclo-(N—O-methyl-L-tryptophanyl-L-isoleucinyl-D-pipecolinyl-L-2-amino-8-oxodecanoyl), is a substance separated from a fungal metabolite, and has been known as an HDAC inhibitor that inhibits cancer cell proliferation through a conventional p21WAF1/Cip1 pathway. The present invention includes not only this apicidin compound, but also a derivative thereof which exhibits a HDAC inhibitory effect in vivo or in vitro.

In the composition of the present invention, the apicidin compound may be prepared as a pharmaceutically acceptable salt and a solvate thereof according to a conventional method in the conventional art. Unless particularly defined otherwise, the "pharmaceutically acceptable salt" includes an acidic or basic salt. For example, as a pharmaceutically acceptable salt, a sodium, calcium or potassium salt of a hydroxyl group is used, and as other pharmaceutically acceptable salts of an amino group, a hydrobromide, a sulfate, hydrogen sulfate, a phosphate, hydrogen phosphate, dihydrogen phosphate, an acetate, a succinate, a citrate, a tartrate, a lactate, a mandelate, methanesulfonate (mesylate) and p-toluenesulfonate (tosylate) may be included. Such pharmaceutically acceptable salts may be prepared by a method or process for preparing a salt, which is known in the art.

In the composition of the present invention, apicidin may be contained at 1 to 100 µM, preferably, 1 to 10 µM, and further preferably 1 to 3 µM. When the concentration of the apicidin is too low, an effect is not exhibited, whereas when the concentration of the apicidin is too high, there is toxicity. Therefore, it is necessary to determine a proper concentration of the apicidin depending on the type of cells.

The term "cardiac-committed cells" used herein refers to all cells included in the process for differentiation of MSCs into cardiomyocytes.

In addition, the present invention provides a method for inducing the differentiation of MSCs into cardiac-committed cells in vitro, which includes treating isolated MSCs with the above-described composition.

In the present invention, there is no particular limitation to the type of MSCs used for the induction of the differentiation into cardiac-committed cells. MSCs may be obtained from known sources, for example, bone marrow, adipose tissue, umbilical cord blood, peripheral blood, etc., and most preferably bone marrow. In addition, animals used for harvesting bone marrow or adipose tissue may be mammals, and when the animal is a human, bone marrow or tissue may be derived from a patient who will be administered with MSCs, as a cell therapeutic agent, which are induced to differentiate due to the treatment of the composition of the present invention, or from others. A method for obtaining MSCs from a known MSC source is well known in the art.

In the present invention, a medium for inducing differentiation may be a medium typically used in the art, and is preferably one or more selected from the group consisting of Minimum Essential Medium alpha (MEM-α), Mesenchymal Stem Cell Growth Medium (MSCGM), and Dulbecco's Modified Eagle's Medium (DMEM).

In addition, the present invention provides a cell therapeutic agent for treating a heart disease, which contains cardiac-committed cells, whose differentiation was induced due to the composition of the present invention, as an active ingredient.

In the present invention, there is no particular limitation to the type of heart disease, and the heart disease may be a cardiovascular disease such as myocardial infarction, angina pectoris, arteriosclerosis or arrhythmia. In addition, the treatment of a heart disease includes alleviation and relief of a heart disease, and improvement of a symptom, and reduction in the likelihood of a heart disease.

The cell therapeutic agent of the present invention may additionally include components including a conventional therapeutically active ingredient, other adjuvants, and pharmaceutically acceptable carriers. Here, the pharmaceutically acceptable carrier is typically used in formulation, and may be, but is not limited to, a saline solution, distilled water, Ringer's solution, buffered saline, a cyclodextrin solution, a dextrose solution, a maltodextrin solution, glycerol, ethanol, or liposomes, etc., and may further include another conventional additive such as an antioxidant or a buffer as needed. In addition, the pharmaceutically acceptable carrier may be formulated as injectable preparations such as an aqueous solution, a suspension, and an emulsion, pills, capsules, granules or tablets by further adding diluents, dispersants, surfactants, binders, lubricants, etc. Suitable pharmaceutically acceptable carriers and their formulation may be prepared according to each ingredient using a method disclosed in the Remington's Pharmaceutical Science. The pharmaceutical composition of the present invention is not limited to a dosage form, and thus may be formulated as injections, inhalants, or external preparations for skin.

The term "subject" refers to a subject in need of treatment, and more specifically, a mammal such as a human, or a non-human primate, a mouse, a rat, a dog, a cat, a horse, and a cow.

In addition, the "pharmaceutically effective amount" used herein may be determined by factors including a disease type, severity of a disease, a patient's age and sex, sensitivity to a drug, administration time, an administration route, an excretion rate, treatment duration, and a simultaneously used drug, and other factors well known in the medical field, and refers to an amount capable of obtaining the maximum effect without side effects, in consideration of all of the factors, which may be easily determined by those of ordinary skill in the art. A daily dose refers to an amount of a therapeutic material of the present invention, which is sufficient for treatment of a disease condition reduced by being administered to a subject in need of treatment. As a non-limiting example, a dosage of the cell therapeutic agent according to the present invention with respect to a human may depend on a patient's age, body weight and sex, an administration type, a health condition, and the severity of a disease, and may be, for example, $1 \times 10^4$ to $1 \times 10^8$ cells/kg.

A method for administering the cell therapeutic agent of the present invention may be, but not particularly limited to, parenteral administration such as intravenous, subcutaneous or intraperitoneal administration, inhalation, skin application or local application, or oral administration according to a therapeutic purpose.

In the present invention, as a result of the comparative evaluation of expression levels of cardiac markers (GATA4, Nkx2.5 and cTnI) after MSCs are treated with HDAC inhibitors (TSA, VPA and AC), it was confirmed that the mRNA/protein expressions of the markers are most significantly increased by apicidin (AC), and it was seen that the apicidin, compared with other HDAC inhibitors, is very effective in the induction of cardiomyogenic differentiation (Examples 2 and 3).

In addition, in the present invention, it was confirmed that, when MSCs are treated with the apicidin, the expression of a nanog, sox2 or oct4 gene, known as a stemness/undifferentiation marker, is inhibited, and it was seen that the apicidin inhibits the maintenance of stem cells in an undifferentiation state and induces an intracellular signal transduction system to initiate differentiation into specific cells (Example 4).

In addition, in the present invention, it was confirmed that when MSCs were treated with the apicidin, the expression of an osteocyte differentiation marker gene (Runx2) and an adipocyte differentiation marker gene (PPAR-γ) is inhibited, and it was able to be seen that the apicidin induces cardiomyocyte-specific differentiation, rather than osteocyte- or adipocyte-specific differentiation (Example 5).

In addition, in the present invention, it was confirmed that when MSCs pretreated with the apicidin are implanted into myocardial infarction mouse models, it was confirmed that cardiomyogenic differentiation is significantly increased in the myocardium, the MSCs treated with the apicidin are induced to differentiate into cardiac-committed cells, and it was seen that after myocardial implantation and engraftment, the MSCs differentiated into cardiomyocytes in a myocardial microenvironment (Example 6).

Hereinafter, to help in understanding the present invention, exemplary examples will be presented. However, the following examples are merely provided to more easily understand the present invention, and not to limit the present invention.

EXAMPLES

Example 1: Isolation and Culture of Human Bone Marrow-Derived MSCs

The bone marrow harvested from a human was diluted with phosphate buffered saline (PBS) at a volume ratio of 1:1 and overlaid on a Ficoll-Hypaque solution (Ficoll-Hypaque, density of 1.077 g/mL, Sigma). Here, the Ficoll-Hypaque solution was kept at room temperature before use, and the volume of the diluted bone marrow was controlled not to exceed 3 times the volume of the Ficoll-Hypaque solution. The diluted bone marrow was centrifuged at a speed of 2,000 rpm for 30 minutes at room temperature, and thus was separated into a red blood cell layer, a mononuclear cell layer and a serum layer. Only the mononuclear cell layer was transferred to a fresh tube using a Pasteur pipette, which was then washed with PBS to remove the Ficoll-Hypaque solution included in harvesting of the mononuclear cell layer or contaminated platelets. This state is called a "mononuclear cell," and to separate and amplify MSCs therefrom, the mononuclear cells were inoculated into low glucose Dulbecco's modified Eagle's medium (DMEM) (Invitrogen-Gibco) containing 10% fetal bovine serum (FBS), 100 units/mL penicillin (Invitiogen-Gibco), and 10 μM/mL of streptomycin (Invitrogen-Gibco) at a concentration of 1 to $2 \times 10^5$ cells/cm$^2$. After 2 to 3 days, non-anchored cells were removed, and monolayer culture was carried out for 2 to 3 weeks, followed by isolation culture of the MSCs.

Afterward, the human bone marrow-derived MSCs were immortalized by lentiviral infection of human telomerase. In the case of primary culture cells, since the lifespan of the cells is limited, as subculture continued, the cell growth capacity and inherent features were changed. Therefore, by introducing the telomerase gene, while an inherent feature such as differentiation capacity was maintained, the lifespan of the cells was sustained, thereby establishing immortalized human bone marrow-derived MSCs.

Example 2: Comparison of Expression of Myocardium-Specific Marker Genes by HDAC Inhibitors To comparatively evaluate whether the apicidin (AC) of the present invention significantly induces the expression of cardiac-specific marker genes (GATA4, Nkx2.5 and cardiac troponin I (cTnI)), compared with trichostatin A (TSA) and valproic acid (VPA), which are widely used as conventional HDAC inhibitors, real-time PCR was performed.

First, MSCs prepared in Example 1 were cultured for one day in a 6-well culture plate containing HIGH glucose/DMEM (4 mM L-glutamine, 4500 mg/L glucose, sodium pyruvate, 10% FBS, 100 U/ml penicillin, 100 μg/ml streptomycin), and then treated with TSA (0.5 μM), VPA (3 mM), and AC (1 and 3 μM) for 24 hours.

Afterward, the cell culture medium was removed from each sample, washed with PBS once, and homogenized with TRIzol for 10 minutes at room temperature, followed by centrifugation after the addition of chloroform. A supernatant obtained by centrifugation was harvested to purify total RNA, and cDNA was synthesized using a reverse transcriptase (MMLV) to be used as a template, followed by real-time PCR performed using the QuantiTect SYBR Green PCR kit. Accordingly, expression levels of the cardiac-specific marker genes (GATA4, Nkx2.5 and cTnI) were confirmed.

Consequently, as shown in FIG. 1, VPA promoted the mRNA expression of GATA4 and cTnI among the cardiac-specific markers, but was not as significantly as effective as AC. TSA had significance only in mRNA expression of cTnI, and no specific effect was exhibited from other cardiac-specific markers (Control: vehicle, Veh). However, the expression of the cardiac-specific markers by AC was most significantly exhibited. Particularly, when AC was added at 3 μM (AC3), it was most effective. Therefore, it can be seen that, compared with other inhibitors, apicidin among the HDAC inhibitors was most effective in the induction of cardiomyogenic differentiation.

Example 3: Induction of Expression of Myocardium-Specific Marker Protein by Apicidin According to Example 2, since it was confirmed that treatment of apicidin (3 μM) provided a most excellent effect of inducing cardiomyogenic differentiation, to further analyze the protein expression of cardiomyogenic differentiation markers by apicidin (3 μM), immunocytochemistry was performed.

First, MSCs were cultured in a 12-well culture plate containing HIGH glucose/DMEM overnight and then treated with 3 μM of AC for 24 hours. Then, the cell culture medium was removed from the sample, and then the cells were washed with PBS once, immobilized on a 3.7% mask foam for 15 minutes to be penetrated with 0.1% Triton X-100 for 10 minutes. After blocking with normal goat serum for 1 hour, the cells were cultured with anti-GATA4, anti-Nkx2.5 and anti-cTnI primary antibodies at 4° C. overnight, and treated with a secondary antibody labeled with a fluorescent dye (Alexa 488, Alexa 594) for 1 hour. After nuclear staining with a fluorescent stain, that is, 4',6-diamidino-2-phenylindole (DAPI) and the cells were mounted and observed using a fluorescent microscope.

Figure 2:
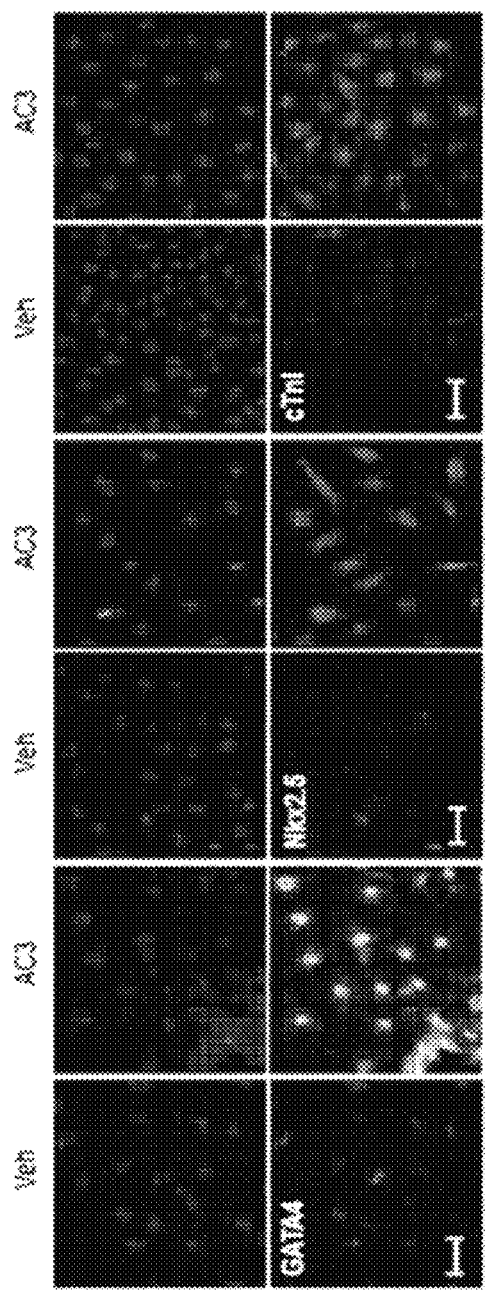
FIG. 2 shows results of immunocytochemistry, showing that the expression of cardiac-specific marker proteins (GATA4, Nkx2.5, and cTnI) is increased when MSCs are treated with apicidin.

Consequently, as shown in FIG. 2, like the result of Example 2, it was confirmed that the intracellular protein expression of the three cardiac-specific markers (GATA4, Nkx2.5 and cTnI) was significantly increased.

Example 4: Effect of Losing Undifferentiation Characteristic of Stem Cells by Apicidin Since it has been known that transcriptional factors such as nanog, sox2 and oct4 are important for maintaining stemness/undifferentiation capacity, when apicidin (3 μM) was treated, to confirm what change occurs in the mRNA expression of these transcriptional factors, real-time PCR was performed.

First, MSCs were cultured in a 12-well culture plate containing HIGH glucose/DMEM overnight and then treated with 3 μM of AC for 24 hours. Then, the cell culture medium was removed from the sample, and then the cells were washed with PBS once, and homogenized with TRIzol for 10 minutes at room temperature, followed by centrifugation after the addition of chloroform. A supernatant obtained by centrifugation was harvested to purify total RNA, and cDNA was synthesized using a reverse transcriptase (MMLV) to be used as a template, followed by real-time PCR performed using the QuantiTect SYBR Green PCR kit. Accordingly, expression levels of the transcriptional factors (nanog, sox2 and oct4) were confirmed.

Figure 3:
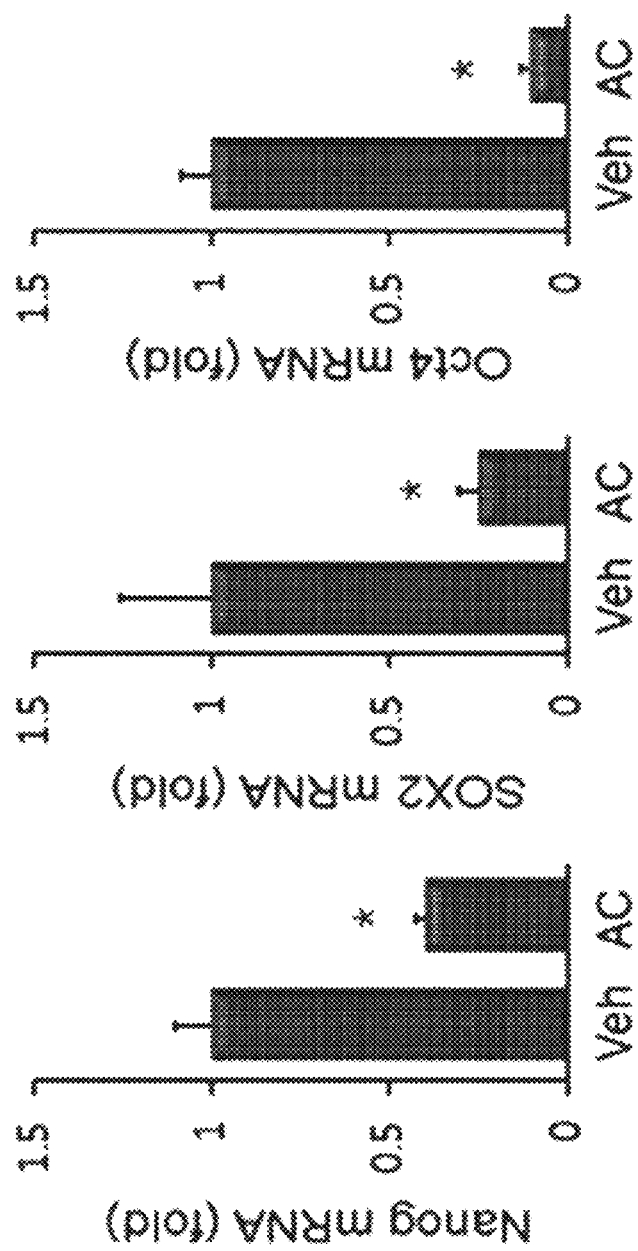
FIG. 3 shows results of real-time PCR, showing that the mRNA expression of stemness/undifferentiation marker genes (nanog, sox2 and oct4) is inhibited when MSCs are treated with apicidin.

Consequently, as shown in FIG. 3, it was able to be seen that the expression of the three factors such as nanog, sox2 and oct4, which are important for maintaining the undifferentiation characteristic of stem cells, was significantly reduced due to treatment of 3 μM AC. Such a result means that the apicidin inhibits the maintenance of an undifferentiation state as stem cells and induces an intracellular signal transduction system that initiates the differentiation into specific cells.

Example 5: Inhibition of Differentiation into Osteocytes (Runx2) and Adipocytes (PPAR-γ) by Apicidin MSCs can differentiate into osteocytes or adipocytes, and here, it is known that Runx2 is expressed in differentiation into osteocytes and is a transcriptional factor that regulates the expression of an osteoblast gene, and PPAR-γ is expressed in differentiation into adipocytes and is a transcriptional factor that regulates the expression of an adipocyte gene. Therefore, when apicidin (3 μM) was treated, to confirm what change occurs in the mRNA expression of these transcriptional factors, real-time PCR was performed.

First, MSCs were cultured in a 12-well culture plate containing HIGH glucose/DMEM overnight and then treated with 3 μM of AC for 24 hours. Then, the cell culture medium was removed from the sample, and then the cells were washed with PBS once, and homogenized with TRIzol for 10 minutes at room temperature, followed by centrifugation after the addition of chloroform. A supernatant obtained by centrifugation was harvested to purify total RNA, and cDNA was synthesized using a reverse transcriptase (MMLV) to be used as a template, followed by real-time PCR performed using the QuantiTect SYBR Green PCR kit. Accordingly, expression levels of an osteocyte differentiation marker (Runx2) and an adipocyte differentiation marker (PPAR-γ) were confirmed.

Figure 4:
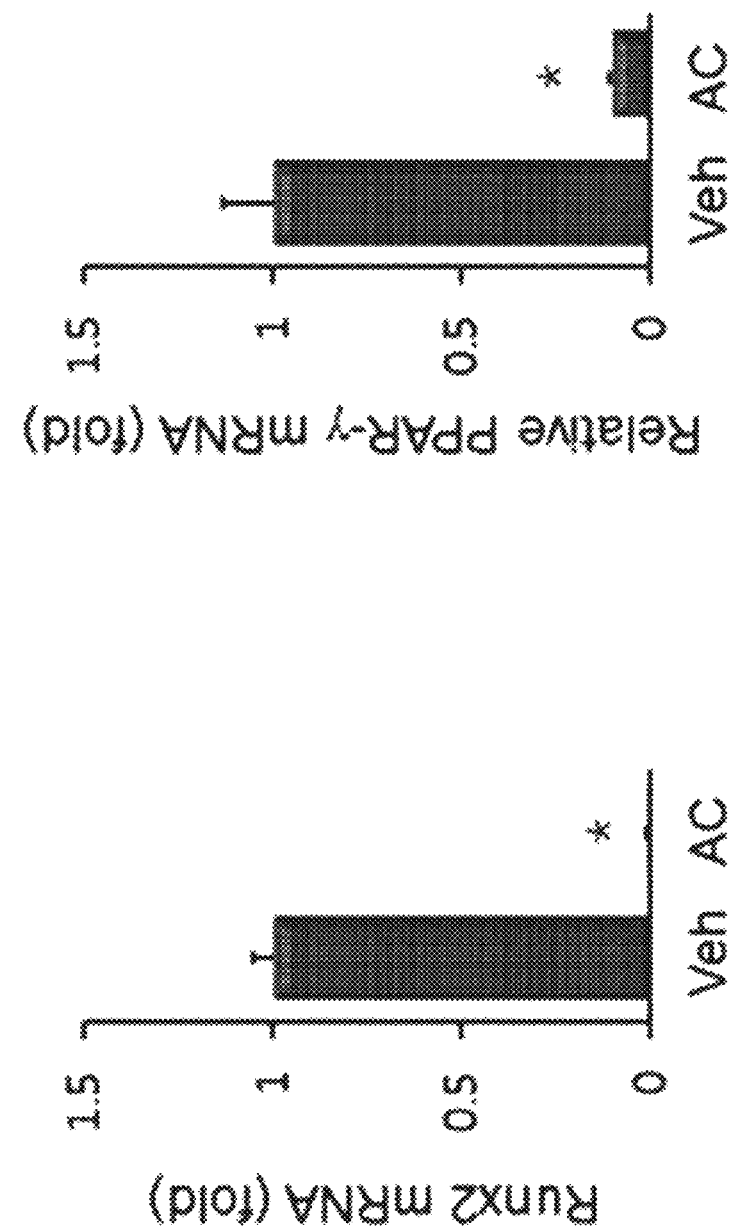
FIG. 4 shows real-time PCR results, confirming that the mRNA expression of an osteocyte differentiation marker gene (Runx2) and an adipocyte differentiation marker gene (PPAR-γ) is inhibited when MSCs are treated with apicidin.

Consequently, as shown in FIG. 4, it was confirmed that, in the MSCs, the expression of the osteocyte differentiation marker (Runx2) or adipocyte differentiation marker (PPAR-γ) was significantly reduced due to treatment of 3 μM of AC. Such a result means that the apicidin inhibits the maintenance of an undifferentiation state as stem cells, and induces cardiomyocyte-specific differentiation, rather than osteocyte- or adipocyte-specific differentiation.

Example 6: Induction of Cardiomyogenic Differentiation in In Vivo Myocardial Infarction Animal Models by Apicidin In addition to the in vitro data of the above examples, when MSCs pretreated with apicidin were implanted even in in vivo myocardial infarction animal models, it was confirmed that cardiomyogenic differentiation was induced in the myocardium. All experimental processes for animal studies were approved by the Animal Experiment Ethics Committee of the Chonnam National University Medical School and performed according to the guidelines and regulations of the Committee on Animal Protection.

First, as a myocardial infarction animal model, an innate immune-deficient mouse, that is, a SCID mouse (BALB/c-nude male mouse, 8-week old) was used, and myocardial infarction was caused by left anterior descending (LAD) coronary occlusion surgery. The mouse was anesthetized with ketamine (50 mg/kg) and xylazine (5 mg/kg), and then the mouse was oxygenated using a ventilator with 95% $O_2$ and 5% $CO_2$. The $3^{rd}$ rib and the $4^{th}$ rib were fixed with a retractor, the chest was opened, and the proximal portion of the left coronary artery under the left atrial appendage was wrapped with a 7-0 silk suture. The skin was closed with a 5-0 silk suture, and the suture site was disinfected.

Seven days after the myocardial infarction, for cell implantation, the MSCs were divided into three groups (① PBS, ② untreated MSCs,untreated MSCs, and ③ AC-treated MSCs), and untreated MSCs and AC-treated MSCs (AC/MSC) were labeled with DAPI. To this end, first, a sterilized DAPI solution was added to a cell culture medium at a final concentration of 50 μg/mL, the cells were washed with PBS four times, each group of cells was suspended in 30 μL of PBS for implantation ($3\times10^5$ cells), a 30-gauge needle was used to inject the cells from the myocardial infarction region to the marginal zone. For the PBS group, the same amount of PBS was injected into the myocardial infarction-induced mice. Two weeks after the cell injection, the mouse was sacrificed to extract the heart, and the heart was frozen with liquid nitrogen. Following frozen-embedding of the heart sample using an O.C.T. compound, the heart tissue was sectioned to a thickness of 10 μm so as to mount sections onto slides for immunohistochemistry.

Figure 5:
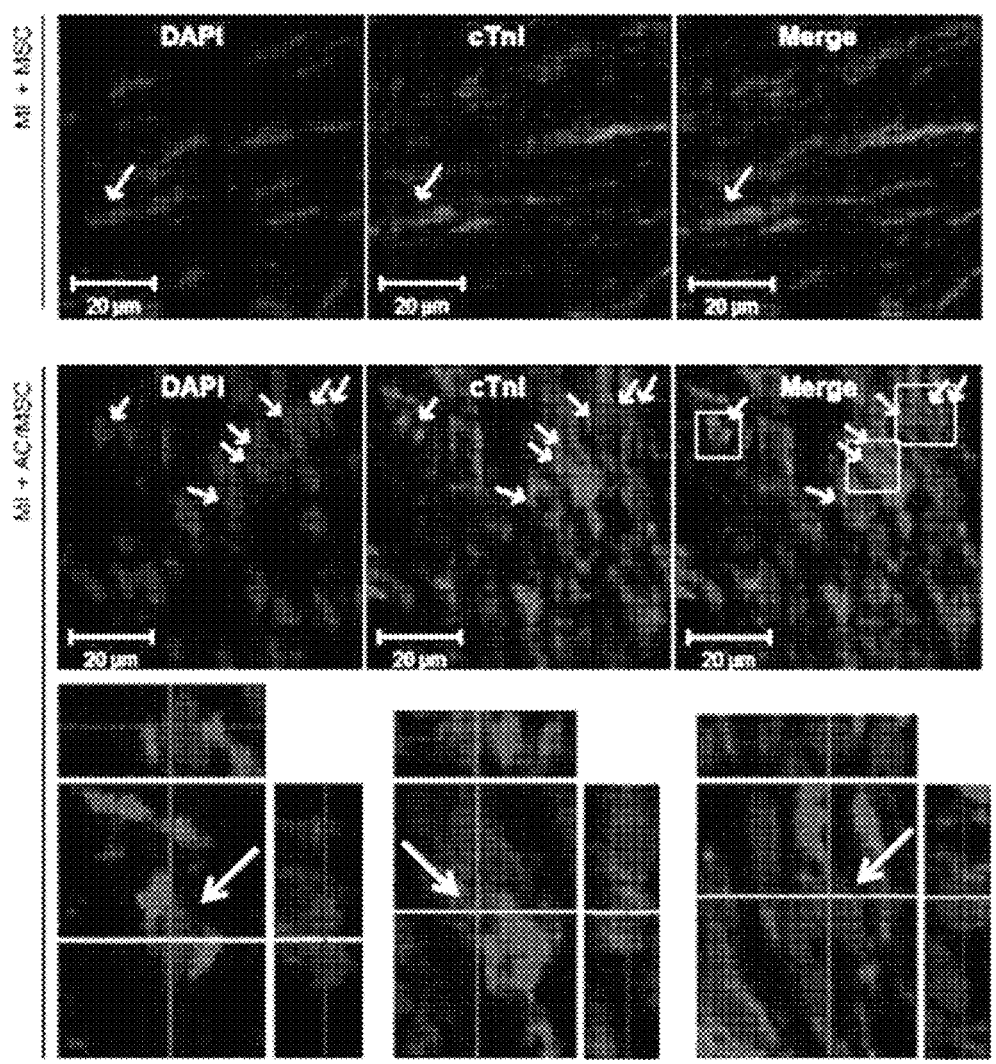
FIG. 5 shows results of immunocytochemistry, showing that cardiomyogenic differentiation in myocardium is significantly increased when MSCs pretreated with apicidin are implanted into myocardial infarction mouse models.

Consequently, as shown in FIG. 5, when the AC-pretreated MSCs (AC/MSC) were implanted, compared with the untreated MSCs that were implanted, the expression of a cardiac-specific structural protein, that is, cardiac troponin I (cTnI) was significantly increased. Such a result shows that the implanted AC-treated MSCs are induced to differentiate into cardiac-committed cells, and after cardiomyogenic differentiation and engraftment, the cells differentiate into cardiomyocytes in a myocardial microenvironment.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

The invention claimed is:

1. A method for inducing the differentiation of mesenchymal stem cells (MSCs) into cardiac-committed cells, comprising:
    treating isolated MSCs with a composition comprising apicidin of Formula 1 below or a pharmaceutically acceptable salt thereof as an active ingredient;
    wherein the MSCs are derived from bone marrow,
    wherein the treating is performed by culturing MSCs in High glucose/DMEM medium, and
    wherein the composition contains apicidin at a concentration of 1 to 3 μM.

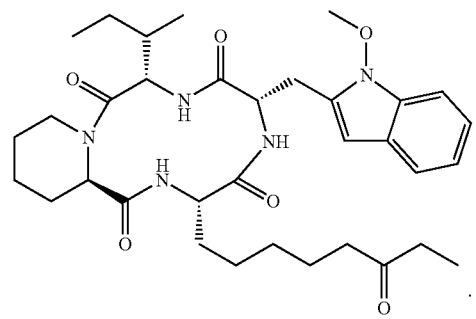 [SMILES: CCC(=O)CCCCC[C@@H]1NC(=O)[C@H]2CCCCN2C(=O)[C@H](C(C)CC)NC(=O)[C@H](Cc2cc3ccccc3n2OC)NC1=O]

2. The method of claim 1, wherein the cardiac-committed cells are for treating a heart disease.

3. The method of claim 2, wherein the heart disease is myocardial infarction, angina pectoris, arteriosclerosis, or arrhythmia.

4. The method of claim 1, wherein the method is for treating a heart disease.

* * * * *